United States Patent
Scheidler-Foegle et al.

(10) Patent No.: US 12,329,836 B2
(45) Date of Patent: Jun. 17, 2025

(54) COMPOSITION COMPRISING AT LEAST ONE AMPS® COPOLYMER, AT LEAST ONE ACYL GLUTAMIC ACID OR A SALT THEREOF AND AT LEAST ONE ALKYL POLYGLUCOSIDE

(71) Applicant: L'OREAL, Paris (FR)

(72) Inventors: Nathalie Scheidler-Foegle, Chevilly la Rue (FR); Maria Helena Rocha Bastien, Chevilly la Rue (FR); Thierry Cotton, Chevilly la Rue (FR)

(73) Assignee: L'OREAL, Paris (FR)

( * ) Notice: Subject to any disclaimer, the term of this patent is extended or adjusted under 35 U.S.C. 154(b) by 680 days.

(21) Appl. No.: 17/615,755

(22) PCT Filed: Jun. 17, 2020

(86) PCT No.: PCT/EP2020/066785
§ 371 (c)(1),
(2) Date: Dec. 1, 2021

(87) PCT Pub. No.: WO2020/254420
PCT Pub. Date: Dec. 24, 2020

(65) Prior Publication Data
US 2022/0304910 A1    Sep. 29, 2022

(30) Foreign Application Priority Data
Jun. 20, 2019 (FR) ...................................... 1906657

(51) Int. Cl.
| | | |
|---|---|---|
| *A61K 8/44* | (2006.01) |
| *A61K 8/60* | (2006.01) |
| *A61K 8/81* | (2006.01) |
| *A61Q 5/00* | (2006.01) |
| *A61Q 19/00* | (2006.01) |

(52) U.S. Cl.
CPC .............. *A61K 8/442* (2013.01); *A61K 8/604* (2013.01); *A61K 8/8158* (2013.01); *A61Q 5/00* (2013.01); *A61Q 19/00* (2013.01); *A61K 2800/10* (2013.01); *A61K 2800/48* (2013.01); *A61K 2800/592* (2013.01)

(58) Field of Classification Search
None
See application file for complete search history.

(56) References Cited

FOREIGN PATENT DOCUMENTS

| | | | |
|---|---|---|---|
| EP | 2 248 508 A2 | 11/2010 | |
| FR | 3007646 A1 * | 1/2015 | ............. A61K 8/375 |

* cited by examiner

*Primary Examiner* — Brian Gulledge
(74) *Attorney, Agent, or Firm* — POLSINELLI PC

(57) ABSTRACT

The present invention relates to a composition comprising at least one copolymer comprising at least one 2-acrylami-do-2-methylpropanesulfonic acid (AMPS®) monomer and at least one monomer bearing a hydrophobic group, at least one acyl glutamic acid or a salt thereof and at least one emulsifying system comprising at least one alkyl polyglucoside.

19 Claims, No Drawings

COMPOSITION COMPRISING AT LEAST ONE AMPS® COPOLYMER, AT LEAST ONE ACYL GLUTAMIC ACID OR A SALT THEREOF AND AT LEAST ONE ALKYL POLYGLUCOSIDE

CROSS REFERENCE TO RELATED APPLICATIONS

This application is a National Phase filing under 35 U.S.C. § 371 of PCT/EP2020/066785 filed on 17 Jun. 2020; which application in turn claims priority to Application No. 1906657 filed in France on 20 Jun. 2019. The entire contents of each application are hereby incorporated by reference.

The present invention relates to a cosmetic composition for the cosmetic treatment of keratin materials. More particularly, the present invention relates to a composition comprising at least one copolymer comprising at least one 2-acrylamido-2-methylpropanesulfonic acid (AMPS®) monomer and at least one monomer bearing a hydrophobic group, at least one acyl glutamic acid or a salt thereof and at least one emulsifying system comprising at least one alkyl polyglucoside.

A subject of the invention is also a process for the cosmetic treatment of keratin materials, in which said composition is applied to said keratin materials.

Another subject of the invention is the use of said composition for the cosmetic treatment of keratin materials.

TECHNICAL FIELD

In the cosmetics field, an increasing number of consumers are looking for cosmetic products of natural origin, while the same time remaining very demanding with regard to the sensory qualities and to the performance quality thereof.

It is therefore necessary to formulate with a maximum of natural ingredients and/or ingredients of natural origin which make it possible to have cosmetic compositions with use qualities that are as close as possible to those of conventional cosmetics.

However, formulae which have a high number of natural ingredients and/or ingredients of natural origin have presentation forms that can cause an impairment to the application to keratin materials. This is because their appearance can be perceived as "pasty" and leading to a soapy effect, also known as whitening effect, on application.

Furthermore, formulae which have a high number of natural ingredients and/or ingredients of natural origin can exhibit problems of stability over time in combination with certain active agents such as anti-ageing agents.

There thus remains the need to provide cosmetic compositions predominantly formulated with natural ingredients and/or ingredients of natural origin that are devoid of the above-mentioned drawbacks.

The term "natural compound" is intended to mean a compound that is obtained directly from the earth or the soil, or from plants or animals, via, where appropriate, one or more physical processes, for instance milling, refining, distillation, purification or filtration.

The term compounds "of natural origin" is intended to mean a natural compound that has undergone one or more additional chemical or industrial treatments, giving rise to modifications that do not affect the essential qualities of this compound and/or a compound predominantly comprising natural constituents that may or may not have undergone transformations as indicated above.

Thus, the aim of the present invention is to develop a cosmetic composition which has good sensory and cosmetic properties, in particular to have a cosmetic composition which has a less pasty appearance and exhibits little or no soaping problem during application, and also good stability over time.

DISCLOSURE OF THE INVENTION

A subject of the present invention is a composition comprising:
 a) at least one copolymer comprising at least one 2-acrylamido-2-methylpropane sulfonic acid (AMPS®) monomer and at least one monomer bearing a hydrophobic group,
 b) at least one acyl glutamic acid or a salt thereof,
 c) at least one emulsifying system comprising at least one alkyl polyglucoside.

The present invention also relates to a process for the cosmetic treatment of keratin materials, comprising the application to said keratin materials of a composition as defined above.

A subject of the invention is also the use of a composition as defined above, for the cosmetic treatment of keratin materials.

Thus, the inventors have demonstrated that a composition comprising at least one AMPS® copolymer in combination with at least one acyl glutamic acid or a salt thereof and an emulsifying system has a softer appearance and is more pleasant to the touch, allowing easy application to keratin materials such as the skin, and reduces, or even eliminates, the problem of soaping during application.

Furthermore, this composition exhibits stability over time in combination with active agents, such as anti-ageing active agents.

The invention is not limited to the illustrated examples. The features of the various examples may in particular be combined within variants which are not illustrated.

The expression "comprising a" should be understood as meaning "comprising at least one", unless otherwise specified.

The expression "at least one" is intended to mean "one or more".

According to the invention, the term "pasty" is intended to mean a composition which has a "viscous" consistency that is difficult to take up and to apply to keratin materials such as the skin.

According to the invention, the term "keratin materials" is intended to mean the skin, of the body, face and/or area around the eyes, the lips, the nails, mucous membranes, the eyelashes, the eyebrows, bodily hair, the scalp and/or the hair, or any other area of bodily skin. More particularly, the keratin materials according to the invention are the scalp, the hair and/or the skin.

Preferably, the keratin materials according to the invention are the skin.

The term "skin" is intended to mean all of the skin of the body, and preferably the skin of the face, neckline, neck, arms and forearms, or even more preferably the skin of the face, in particular of the forehead, nose, cheeks, chin and area around the eyes.

The term "copolymer" is intended to mean both copolymers obtained from two types of monomer and those obtained from more than two types of monomer, such as terpolymers obtained from three types of monomer.

Preferably, the composition according to the invention is a cosmetic composition, more preferentially a cosmetic composition for the treatment of keratin materials such as the skin.

AMPS® Copolymer

The composition according to the invention comprises at least one 2-acrylamido-2-methylpropane sulfonic acid (AMPS®) monomer and at least one monomer bearing a hydrophobic group.

Within the context of the present invention, the term "hydrophobic group" is understood to be a hydrocarbon-based, branched or unbranched, saturated or unsaturated fatty chain comprising from 6 to 50 carbon atoms.

The AMPS® copolymer(s) may be crosslinked. When they are crosslinked, the crosslinking agents can be chosen from polyolefinically unsaturated compounds commonly used for the crosslinking of polymers obtained by radical polymerization.

The term "crosslinked copolymer" is understood to be a non-linear copolymer which is in the form of a three-dimensional network that is insoluble in water but swellable in water, leading to the production of a chemical gel.

The crosslinking agent is more particularly chosen from ethylene glycol dimethacrylate, tetraallyloxyethane, ethylene glycol diacrylate, diallylurea, triallylamine, trimethylolpropane triacrylate or methylenebisacrylamide, or a mixture of these compounds. Preferably, the crosslinking agent is trimethylolpropane triacrylate.

Preferably, the AMPS® copolymer(s) are crosslinked by a crosslinking agent, preferably trimethylolpropane triacrylate.

The 2-acrylamido-2-methylpropanesulfonic acid monomer(s) of the copolymer contained in the composition in accordance with the invention are in free form or are partially or totally neutralized with a mineral base (sodium hydroxide, potassium hydroxide or aqueous ammonia) or an organic base, such as mono-, di- or triethanolamine, an aminomethylpropanediol, N-methylglucamine, basic amino acids, such as arginine and lysine, and the mixture of these compounds.

According to the invention, the 2-acrylamido-2-methylpropane sulfonic acid (AMPS®) monomers preferably correspond to general formula (I) below:

[Chem. 1]

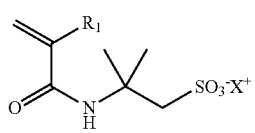

(I)

in which $X^+$ denotes a cationic counterion, in particular an alkali metal or alkaline-earth metal, or an ammonium, preferably ammonium, or a mixture of cations; $R_1$ denotes a hydrogen atom or a linear or branched $C_1$-$C_6$ alkyl radical such as methyl, and $R_1$ preferably denotes a hydrogen atom.

Preferably, the 2-acrylamido-2-methylpropane sulfonic acid monomer(s) according to the invention are partially or completely salified in the form of the ammonium salt.

More preferentially, the 2-acrylamido-2-methylpropane sulfonic acid monomer(s) according to the invention are completely salified, preferably in the form of the ammonium salt.

The AMPS® copolymer(s) comprise at least one monomer bearing a hydrophobic group which is preferably an ethylenically unsaturated monomer comprising at least one fatty hydrocarbon-based chain part comprising from 6 to 50 carbon atoms, preferably from 6 to 22 and more particularly from 12 to 18 carbon atoms.

This ethylenically unsaturated hydrophobic monomer is preferably chosen from the acrylates or acrylamides of formula (II):

[Chem. 2]

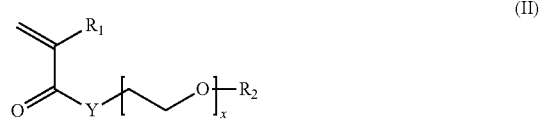

(II)

in which $R_1$ denotes a hydrogen atom or a linear or branched $C_1$-$C_6$ alkyl radical, preferably methyl; Y denotes O or NH; $R_2$ denotes a hydrophobic hydrocarbon-based radical comprising from 6 to 50 carbon atoms, more preferentially from 6 to 22 carbon atoms and even more preferentially from 12 to 18 carbon atoms; x denotes a number ranging from 0 to 100.

According to one preferred embodiment of the invention, in formula (II), Y denotes an oxygen atom.

According to one preferred embodiment of the invention, in formula (II), the group $R_1$ represents a methyl.

According to one particular embodiment of the invention, x represents an integer between 3 and 25.

According to one preferred embodiment of the invention, in formula (II), the group $R_2$ represents an alkyl radical comprising from 12 to 18 carbon atoms.

According to an even more preferred embodiment of the invention, in formula (II), Y denotes an oxygen atom, the group $R_1$ represents a methyl, the group $R_2$ represents an alkyl radical comprising from 12 to 18 carbon atoms, and x represents an integer between 3 and 25.

Preferably, the monomer bearing a hydrophobic group of formula (II) is ethoxylated (25EO) stearyl methacrylate, corresponding to the compound of formula (II) in which the group $R_1$ represents a methyl, the group Y denotes O, the group $R_2$ represents an alkyl radical comprising 18 carbon atoms and x is equal to 25.

According to one particular embodiment of the invention, the monomer bearing a hydrophobic group of formula (II) is tetraethoxylated (4EO) lauryl methacrylate, corresponding to the compound of formula (II) in which the group $R_1$ represents a methyl, the group Y denotes O, the group $R_2$ represents an alkyl radical comprising 12 carbon atoms and x is equal to 4.

In this embodiment, the monomer bearing a hydrophobic group is preferably tetraethoxylated lauryl methacrylate.

According to another particular embodiment of the invention, the AMPS® copolymer may comprise at least one monomer of formula (II) in which x is equal to 0, with Y preferably denoting an oxygen atom, the group $R_1$ representing a methyl, and the group $R_2$ representing an alkyl radical comprising from 12 to 18 carbon atoms.

In this embodiment, the monomer bearing a hydrophobic group is preferably lauryl methacrylate.

According to another particular embodiment, the AMPS® copolymer comprises at least one monomer of formula (II) in which x is equal to 0, with Y preferably denoting an oxygen atom, the group $R_1$ representing a methyl, and the group $R_2$ representing an alkyl radical comprising from 12 to 18 carbon atoms, and at least one monomer of formula (II)

in which Y denotes an oxygen atom, the group $R_1$ represents a methyl, the group $R_2$ represents an alkyl radical comprising from 12 to 18 carbon atoms, and x represents an integer between 3 and 25, and x is preferably equal to 4.

In this embodiment, the AMPS® copolymer preferably comprises, as monomers bearing a hydrophobic group, lauryl methacrylate and tetraethoxylated lauryl methacrylate.

Preferably, the monomer bearing a hydrophobic group is ethoxylated (25EO) lauryl methacrylate.

According to a particular embodiment of the invention, the AMPS® copolymer may also comprise at least one ethylenically unsaturated monomer which does not comprise any hydrophobic groups, preferably corresponding to the general formula (III) below:
[Chem. 3]

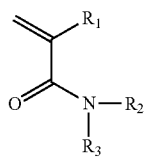

(III)

in which $R_1$ denotes a hydrogen atom or a linear or branched $C_1$-$C_4$ alkyl radical, $R_1$ preferably denotes a hydrogen atom, $R_2$ denotes a linear or branched $C_1$-$C_4$ alkyl radical and $R_3$ denotes a linear or branched $C_1$-$C_4$ alkyl radical and $R_2$ and $R_3$ preferably denote a methyl.

The ethylenically unsaturated monomer which does not comprise any hydrophobic groups is chosen from (meth)acrylamides such as acrylamide, (meth)acrylic acids and the esters ((meth)acrylates) thereof, such as 2-hydroxyethyl acrylate, vinylpyrrolidones, N—($C_1$-$C_4$)alkylacrylamides, and N,N-di($C_1$-$C_4$)alkylacrylamides such as N,N-dimethylacrylamide.

In this embodiment, the ethylenically unsaturated monomer which does not comprise any hydrophobic groups is preferably N,N-dimethylacrylamide.

Preferably, the AMPS® copolymer is a copolymer of 2-acrylamido-2-methylpropanesulfonic acid which is preferably totally salified, preferably in the form of an ammonium salt, and of ethoxylated (25EO) stearyl methacrylate.

As AMPS® copolymer, mention may be made of the copolymer sold under the reference Aristoflex HMS by the company Clariant, of INCI name Ammonium acryloyldimethyltaurate/steareth-25 methacrylate crosspolymer.

The AMPS® copolymer(s) described above may be present in the composition in a content ranging from 0.01% to 10% by weight, more preferentially from 0.05% to 5% by weight and even more preferentially from 0.1% to 2% by weight, relative to the total weight of the composition.

Acyl Glutamic Acid and Salts Thereof

The composition according to the invention comprises at least one acyl glutamic acid (INCI name: acyl glutamic acid) or a salt thereof (acyl glutamates).

Preferably, the acyl glutamic acid(s) are chosen from acyl glutamic acids in which the acyl group comprises from 10 to 30 carbon atoms, preferably from 12 to 22 carbon atoms, such as lauroylglutamic acid, myristoylglutamic acid, palmitoylglutamic acid, stearoylglutamic acid, behenoylglutamic acid, olivoylglutamic acid, cocoylglutamic acid, and the salts of these acids, especially the salts of alkali metals such as Na, Li or K, preferably Na or K, the salts of alkaline-earth metals such as Mg, or the ammonium salts of said acids.

Preferably, the acyl glutamic acid(s) or a salt thereof are chosen from lauroylglutamic acids, cocoylglutamic acids, sodium stearoyl glutamate, potassium lauroyl glutamate, potassium cocoyl glutamate, sodium olivoyl glutamate and mixtures thereof.

More preferentially, the acyl glutamic acid or a salt thereof is sodium stearoyl glutamate (INCI name).

Such compounds are sold under the name Amisoft by the company Ajinomoto and in particular under the references Amisoft CA, Amisoft LA, Amisoft HS 11 PF, Amisoft MK-11, Amisoft LK-11 and Amisoft CK-11, or alternatively under the name Eumulgin SG by the company Cognis.

Mention may also be made of triethanolamine cocoyl glutamate sold under the name Amisoft CT12 by the company Ajinomoto, and triethanolamine lauroyl glutamate sold under the name Acylglutamate LT-12 by the company Ajinomoto.

As acyl glutamic acid salt, mention may also be made of sodium hydrogenated tallowoyl glutamate, such as the product sold under the reference Acylglutamate HS 11 by the company Ajinomoto and disodium hydrogenated tallow glutamate, such as the product sold under the reference Acylglutamate HS-21 by the company Ajinomoto.

Mention may also be made of commercial mixtures of surfactants comprising at least one glutamic acid derivative or a salt of said derivative, for instance the mixture of acyl glutamate salts such as Amisoft LS-22 sold by Ajinomoto.

According to one preferred embodiment of the invention, the monosodium salt of n-stearoyl-L-glutamic acid (INCI name: sodium stearoyl glutamate), such as the product sold by the company Ajinomoto under the reference Amisoft HS 11 PF, is used.

The acyl glutamic acid(s) and salts thereof may be present in the composition in a content ranging from 0.01% to 5% by weight, preferably from 0.01% to 2% by weight, more preferentially from 0.01% to 1% by weight, relative to the total weight of the composition.

Emulsifying System

The composition according to the invention comprises an emulsifying system comprising at least one alkyl polyglucoside.

The term "emulsifying system" is intended to mean a system capable of forming an emulsion comprising surfactants.

For the purposes of the present invention, the term "alkyl polyglucoside" is intended to mean an alkylmonosaccharide (degree of polymerization 1) or an alkyl polysaccharide (degree of polymerization greater than 1).

The alkyl polyglucosides may be used alone or in the form of mixtures of several alkyl polyglucosides. They generally correspond to formula (IV) below:
[Chem. 4]

$$R_1O\text{-}(G)_a \quad\quad (IV)$$

in which:
the radical $R_1$ denotes a linear or branched alkyl radical comprising from 6 to 30 carbon atoms, preferably from 6 to 24 carbon atoms, more preferentially from 8 to 22, and even more preferentially from 12 to 20;
the group G is a saccharide residue;
a is a number ranging from 1 to 10.

Examples of alkyl polyglucosides that may be mentioned include decyl glucoside, for instance the product sold under the name Mydol 10® by the company Kao Chemicals or the product sold under the name Plantacare 2000 UP® by the company Henkel or the product sold under the name Oramix NS 10® by the company SEPPIC; caprylyl/capryl glucoside, for instance the product sold under the name Plantacare KE 3711® by the company Cognis or Oramix CG 110® by the company SEPPIC; lauryl glucoside, for instance the product sold under the name Plantacare 1200 UP® by the company Henkel or Plantaren 1200 N® by the company Henkel; cetearyl glucoside optionally as a mixture with cetostearyl alcohol, for example sold under the name Montanov 68 by the company SEPPIC, under the name Tego Care CG90 by the company Evonik Goldschmidt and under the names Emulgade PL1618 or Emulgade KE 3302 by the company Cognis; arachidyl glucoside, for example in the form of a mixture of arachidyl and behenyl alcohols and of arachidyl glucoside, sold under the name Montanov 202 by the company SEPPIC; cocoglucoside such as the product sold under the name Plantacare 818 UP® by the company Henkel; or the product in the form of a mixture of cocyl polyglucoside and of cetyl and stearyl alcohols (35/65) sold under the name Montanov 82 by the company SEPPIC; methyl cocoyl glucoside sold under the name Eumulgin GTS by the company Cognis; octyldodecyl xyloside sold, for example, under the names Fluidanov 20X or Easynov by the company SEPPIC; caprylyl glucoside, for instance the product sold under the name Plantacare 810 UP® by the company Cognis; and mixtures thereof.

According to one preferred embodiment of the invention, the radical $R_1$ denotes a linear or branched alkyl radical comprising from 6 to 24 carbon atoms, preferably from 8 to 22, and even more preferentially from 12 to 20.

According to another preferred embodiment of the invention, $(G)_a$ is a glucoside group comprising from 1 to 5 and especially 1.2 to 3 glucoside units.

Preferably, the alkyl polyglucoside(s) correspond to formula (V) below:
[Chem. 5]

$$RO\text{-}(G)_x \quad (V)$$

in which:
the radical R denotes a linear or branched alkyl radical comprising from 12 to 22 carbon atoms;
the group G is a saccharide residue;
x ranges from 1 to 5, preferably from 1.05 to 2.5 and even more preferentially from 1.1 to 2.

The saccharide residue may be chosen from glucose, dextrose, saccharose, fructose, galactose, maltose, maltotriose, lactose, cellobiose, mannose, ribose, dextran, talose, allose, xylose, levoglucan, cellulose and starch, and mixtures thereof. More preferentially, the saccharide residue is glucose.

It should also be noted that each unit of the polysaccharide part of the alkyl polyglucoside may be in α or β isomer form, in L or D form, and the configuration of the saccharide residue may be of furanoside or pyranoside type.

It is, of course, possible to use mixtures of alkyl polysaccharides, which may differ from one another in the nature of the borne alkyl unit and/or the nature of the bearing polysaccharide chain.

According to one preferred embodiment of the invention, the alkyl polyglucoside may be used as a mixture with at least one fatty alcohol, especially a fatty alcohol containing from 10 to 30 carbon atoms and more particularly from 12 to 22 carbon atoms.

In addition, it is particularly advantageous, according to the present invention, to use together a fatty alcohol and an alkyl polyglucoside of which the alkyl part is identical to that of the selected fatty alcohol.

The fatty alcohol/alkyl polyglucoside emulsifying mixtures as defined above are known as such. They are described especially in applications WO92/06778, WO95/13863 and WO98/47610 and prepared according to the preparation processes indicated in these documents.

Among the particularly preferred fatty alcohols/alkyl polyglucoside mixtures, mention may be made of the products sold by the company SEPPIC under the name Montanov®, such as the following mixtures:
cetylstearyl alcohol/cocoyl glucoside—Montanov 82®,
arachidyl alcohol and behenyl alcohol/arachidyl glucoside—Montanov 202®,
myristyl alcohol/myristyl glucoside—Montanov 14®,
cetylstearyl alcohol/cetylstearyl glucoside—Montanov 68®,
$C_{14}$-$C_{22}$ alcohol/$C_{12}$-$C_{20}$ alkyl glucoside—Montanov® L®,
cocoyl alcohol/cocoyl glucoside—Montanov S®,
isostearyl alcohol/isostearyl glucoside—Montanov WO 18®.

Preferably, the alkyl polyglucoside(s) employed in the composition according to the invention are chosen from cetylstearyl glucoside, arachidyl glucoside and mixtures thereof.

Preferably, the alkyl polyglucoside(s) employed in the composition according to the invention are used in the form of a mixture with a fatty alcohol chosen from cetylstearyl alcohol (also called cetearyl alcohol), arachidyl alcohol, behenyl alcohol and mixtures thereof.

Preferably, the alkyl polyglucoside(s) are chosen from the arachidyl alcohol and behenyl alcohol/arachidyl glucoside mixture, the cetylstearyl alcohol/cetylstearyl glucoside mixture, and mixtures thereof.

Preferably, the composition according to the invention comprises an emulsifying system comprising at least one alkyl polyglucoside chosen from the arachidyl alcohol and behenyl alcohol/arachidyl glucoside mixture, the cetylstearyl alcohol/cetylstearyl glucoside mixture, and mixtures thereof.

Mention may be made of the cetylstearyl alcohol/cetylstearyl glucoside mixture, sold by the company SEPPIC under the name Montanov 68®, constituted of approximately 20% of cetylstearyl glucoside and approximately 80% of cetylstearyl alcohol Mention may also be made of the arachidyl alcohol and behenyl alcohol/arachidyl glucoside mixture sold by the company SEPPIC under the name Montanov 202®.

The alkyl polyglucoside(s) may be present in the composition according to the invention in a content ranging from 0.01% to 15% by weight, preferably from 0.1% to 10% by weight, relative to the total weight of the composition.

Fatty Substance:

The composition according to the invention may comprise at least one fatty substance.

The term "fatty substance" is intended to mean an organic compound that is insoluble in water at ordinary ambient temperature (25° C.) and at atmospheric pressure (760 mmHg) (solubility of less than 5%, preferably less than 1% and even more preferentially less than 0.1%). They have in their structure at least one hydrocarbon-based chain comprising at least 6 carbon atoms or a sequence of at least two siloxane groups. In addition, the fatty substances are generally soluble in organic solvents under the same temperature and pressure conditions, for instance chloroform, ethanol, benzene, liquid petroleum jelly or decamethylcyclopentasiloxane.

These fatty substances are neither polyoxyethylenated nor polyglycerolated.

Preferably, the fatty substance(s) are in particular chosen from $C_6$-$C_{16}$ alkanes, oils of animal origin, oils of plant origin, glycerides, fluoro oils of synthetic origin, fatty alcohols, fatty acid and/or fatty alcohol esters, non-silicone waxes, and silicones, and mixtures thereof.

It is recalled that, for the purposes of the invention, the fatty alcohols, fatty esters and fatty acids more particularly contain one or more linear or branched, saturated or unsaturated hydrocarbon-based groups comprising 6 to 30 carbon atoms, which are optionally substituted, in particular with one or more (in particular 1 to 4) hydroxyl groups. If they are unsaturated, these compounds may comprise one to three conjugated or unconjugated carbon-carbon double bonds.

As regards the $C_6$-$C_{16}$ alkanes, they may be linear or branched, and possibly cyclic. Examples that may be mentioned include hexane, dodecane and isoparaffins such as isohexadecane and isodecane. The linear or branched hydrocarbons containing more than 16 carbon atoms may be chosen from liquid paraffins, petroleum jelly, liquid petroleum jelly, polydecenes, and hydrogenated polyisobutene such as Parleam®.

According to one particular embodiment, the fatty substance(s) used in the composition of the invention are chosen from volatile linear alkanes.

The term "one or more volatile linear alkanes" is intended to mean, without distinction, "one or more volatile linear alkane oils".

A volatile linear alkane that is suitable for the invention is liquid at ambient temperature (about 25° C.) and atmospheric pressure (101 325 Pa or 760 mmHg).

The term "volatile linear alkane" that is suitable for the invention is intended to mean a linear alkane that can evaporate on contact with the skin in less than one hour, at ambient temperature (25° C.) and atmospheric pressure (101 325 Pa), which is liquid at ambient temperature, in particular having an evaporation rate ranging from 0.01 to 15 mg/cm²/minute, at ambient temperature (25° C.) and atmospheric pressure (101 325 Pa).

Preferably, the volatile linear alkanes that are suitable for the invention have an evaporation rate ranging from 0.01 to 3.5 mg/cm²/minute and better still from 0.01 to 1.5 mg/cm²/minute, at ambient temperature (25° C.) and atmospheric pressure (101 325 Pa).

More preferably, the volatile linear alkanes that are suitable for the invention have an evaporation rate ranging from 0.01 to 0.8 mg/cm²/minute, preferentially from 0.01 to 0.3 mg/cm²/minute and even more preferentially from 0.01 to 0.12 mg/cm²/minute, at ambient temperature (25° C.) and atmospheric pressure (101 325 Pa).

The evaporation rate of a volatile alkane in accordance with the invention (and more generally of a volatile solvent) may in particular be evaluated by means of the protocol described in WO 06/013 413, and more particularly by means of the protocol described below.

15 g of volatile hydrocarbon-based solvent are placed in a crystallizing dish (diameter: 7 cm) placed on a balance that is in a chamber of about 0.3 m³ which is temperature-regulated (25° C.) and hygrometry-regulated (50% relative humidity).

The volatile hydrocarbon-based solvent is allowed to evaporate freely, without stirring it, while providing ventilation by means of a fan (Papst-Motoren, reference 8550 N, rotating at 2700 rpm) placed in a vertical position above the crystallizing dish containing the volatile hydrocarbon-based solvent, the blades being directed towards the crystallizing dish, 20 cm away from the bottom of the crystallizing dish.

The weight of volatile hydrocarbon-based solvent remaining in the crystallizing dish is measured at regular time intervals. The evaporation profile of the solvent is then obtained by plotting the curve of the amount of product evaporated (in mg/cm²) as a function of the time (in minutes).

The evaporation rate is then calculated, which corresponds to the tangent to the origin of the curve obtained. The evaporation rates are expressed in mg of volatile solvent evaporated per unit of surface area (cm²) and per unit of time (minute).

According to one preferred embodiment, the volatile linear alkanes that are suitable for the invention have a non-zero vapour pressure (also known as saturation vapour pressure), at ambient temperature, in particular a vapour pressure ranging from 0.3 Pa to 6000 Pa.

Preferably, the volatile linear alkanes that are suitable for the invention have a vapour pressure ranging from 0.3 to 2000 Pa and better still from 0.3 to 1000 Pa, at ambient temperature (25° C.). More preferably, the volatile linear alkanes that are suitable for the invention have a vapour pressure ranging from 0.4 to 600 Pa, preferentially from 1 to 200 Pa and even more preferentially from 3 to 60 Pa, at ambient temperature (25° C.).

A volatile linear alkane that is suitable for the invention may have a flash point that is within the range from 30 to 120° C. and more particularly from 40 to 100° C. The flash point is in particular measured according to standard ISO 3679.

The volatile linear alkanes that are suitable for the invention may be linear alkanes comprising from 7 to 15 carbon atoms, preferably from 8 to 14 carbon atoms and better still from 9 to 14 carbon atoms.

A volatile linear alkane that is suitable for the invention may advantageously be of plant origin.

As examples of alkanes that are suitable for the invention, mention may be made of the alkanes described in patent applications WO 2007/068371 and WO 2008/155059. These alkanes are obtained from fatty alcohols, which are themselves obtained from coconut oil or palm oil.

As examples of linear alkanes that are suitable for the invention, mention may be made of n-heptane (C7), n-octane (C8), n-nonane (C9), n-decane (C10), n-undecane (C11), n-dodecane (C12), n-tridecane (C13), n-tetradecane (C14), and n-pentadecane (C15) and mixtures thereof. According to a particular embodiment, the volatile linear alkane is chosen from n-nonane, n-undecane, n-dodecane, n-tridecane and n-tetradecane, and mixtures thereof.

According to one preferred embodiment, mention may be made of mixtures of n-undecane (C11) and of n-tridecane (C13) obtained in Examples 1 and 2 of application WO 2008/155059.

Mention may also be made of n-dodecane (C12) and n-tetradecane (C14) sold, respectively, under the references Parafol 12-97 and Parafol 14-97 by the company Sasol, and also mixtures thereof.

One embodiment consists in using only one volatile linear alkane. Alternatively, a mixture of at least two different volatile linear alkanes, differing from one another by a carbon number n of at least 1, in particular differing from one another by a carbon number of 1 or 2, may be used.

Among the animal oils, mention may be made of perhydrosqualene.

Among the triglycerides of plant or synthetic origin, mention may be made of liquid fatty acid triglycerides comprising from 6 to 30 carbon atoms, for instance heptanoic or octanoic acid triglycerides, or alternatively, for example, sunflower oil, maize oil, soybean oil, marrow oil, grapeseed oil, sesame oil, hazelnut oil, apricot oil, macadamia oil, arara oil, sunflower oil, castor oil, avocado oil, coconut oil, coriander oil, jojoba oil, shea butter oil and caprylic/capric acid triglycerides, for instance those sold by Stéarineries Dubois or those sold under the names Miglyol® 810, 812 and 818 by Dynamit Nobel.

Fluoro oils that may be mentioned include perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or alternatively bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols that may be used in the cosmetic compositions of the invention are saturated or unsaturated, and linear or branched, and comprise from 6 to 30 carbon atoms and more particularly from 8 to 30 carbon atoms. Examples that may be mentioned include cetyl alcohol, stearyl alcohol and the mixture thereof (cetylstearyl alcohol), octyldodecanol, 2-butyloctanol, 2-hexyldecanol, 2-undecylpentadecanol, oleyl alcohol and linoleyl alcohol.

The wax(es) that may be used in the cosmetic composition of the invention are chosen especially from carnauba wax, candelilla wax, esparto grass wax, paraffin wax, ozokerite, plant waxes, for instance olive tree wax, rice wax, hydrogenated jojoba wax or the absolute waxes of flowers such as the essential wax of blackcurrant blossom sold by the company Bertin (France), animal waxes, for instance beeswaxes, or modified beeswaxes (cerabellina); other waxes or waxy starting materials that may be used according to the invention are especially marine waxes such as the product sold by the company Sophim under the reference M82, and polyethylene waxes or polyolefin waxes in general.

As regards the fatty acid and/or fatty alcohol esters, which are advantageously different from the triglycerides mentioned above, mention may be made in particular of esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters more particularly being greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononanoate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

Still within the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

Mention may in particular be made of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisanonate; and polyethylene glycol distearates.

Among the esters mentioned above, it is preferred to use ethyl, isopropyl, myristyl, cetyl or stearyl palmitates, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate or cetyl octanoate.

The composition may also comprise, as fatty ester, sugar esters and diesters of $C_6$-$C_{30}$ and preferably $C_{12}$-$C_{22}$ fatty acids. It is recalled that the term "sugar" is intended to mean oxygen-bearing hydrocarbon-based compounds bearing several alcohol functions, with or without aldehyde or ketone functions, and which include at least 4 carbon atoms. These sugars may be monosaccharides, oligosaccharides or polysaccharides.

Examples of suitable sugars that may be mentioned include sucrose, glucose, galactose, ribose, fucose, maltose, fructose, mannose, arabinose, xylose and lactose, and derivatives thereof, in particular alkyl derivatives, such as methyl derivatives, for instance methylglucose.

The esters of sugars and of fatty acids may be in particular chosen from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds.

The esters according to this variant may also be chosen from mono-, di-, tri- and tetraesters, polyesters, and mixtures thereof.

These esters may be, for example, oleates, laurates, palmitates, myristates, behenates, cocoates, stearates, linoleates, linolenates, caprates and arachidonates, or mixtures thereof such as, in particular, oleopalmitate, oleostearate and palmitostearate mixed esters.

More particularly, use is made of monoesters and diesters and especially sucrose, glucose or methylglucose monooleate or dioleate, stearate, behenate, oleopalmitate, linoleate, linolenate or oleostearate.

The silicones that may be used in the present composition are volatile or non-volatile, cyclic, linear or branched silicones, which are unmodified or modified with organic groups, having a viscosity from $5\times10^{-6}$ to 2.5 m$^2$/s at 25° C., and preferably $1\times10^{-5}$ to 1 m$^2$/s.

The silicones that may be used in accordance with the invention may be in the form of oils, waxes, resins or gums, preferably silicone oils.

Preferably, the silicone(s) are chosen from polydialkylsiloxanes, in particular polydimethylsiloxanes (PDMSs), and organomodified polysiloxanes comprising at least one functional group chosen from poly(oxyethylene) groups, amino groups and alkoxy groups.

The fatty substance(s) may be present in the composition according to the invention in a content ranging from 0.1% to 50% by weight, preferably from 5% to 40% by weight and more preferentially from 5% to 35% by weight relative to the total weight of the composition.

Crosslinked (Meth)Acrylic Acid Homopolymer

The composition according to the invention may comprise at least one crosslinked (meth)acrylic acid homopolymer, different from the AMPS® copolymer described above.

Preferably, the composition according to the invention comprises at least one crosslinked (meth)acrylic acid homopolymer.

The homopolymer may be crosslinked with a crosslinking agent, chosen especially from pentaerythrityl allyl ether, sucrose allyl ether and propylene allyl ether.

Examples that may be mentioned include the products sold by the company Lubrizol under the names Carbopol 910, 934, 940, 941, 934 P, 980, 981, 2984, 5984 and Carbopol Ultrez 10 Polymer (INCI name: carbomer), or by the company 3V-Sigma under the name Synthalen® K, Synthalen® L or Synthalen® M.

The crosslinked (meth)acrylic acid homopolymers, different from the AMPS® copolymer described above, may be present in the composition according to the invention in a content ranging from 0.01% to 5% by weight, preferably from 0.1% to 2% by weight, relative to the total weight of the composition.

Gelling Agent

The composition according to the invention may comprise at least one hydrophilic gelling agent, different from the AMPS® copolymer described above.

Preferably, the hydrophilic gelling agent is chosen from polysaccharides of natural origin, preferably of plant origin, polysaccharides of biotechnological origin, and mixtures thereof.

As an example of polysaccharides of biotechnological origin, mention may be made of xanthan gum.

The plant-derived polysaccharide(s) may, where appropriate, be chemically modified to promote their hydrophilic valency, as is the case for cellulose derivatives, in particular hydroxyalkylcelluloses (e.g.: hydroxyethylcellulose).

As examples of polysaccharides of plant origin that may be used according to the invention, mention may be made especially of:
- algal extracts such as alginates, carrageenans and agar-agar, and mixtures thereof. Examples of carrageenans that may be mentioned include Satiagum UTC30® and UTC10® from the company Cargill; an alginate that may be mentioned is the sodium alginate sold under the name Kelcosol® by the company ISP;
- gums, such guar gum and non-ionic derivatives thereof (hydroxypropyl guar), gum arabic, konjac gum or mannan gum, gum tragacanth, ghatti gum, karaya gum, locust bean gum; examples that may be mentioned include the guar gum sold under the name Jaguar HP 105® by the company Rhodia; mannan gum and Konjac Gum® (1% glucomannan) sold by the company GfN;
- modified or unmodified starches, such as those derived, for example, from cereals such as wheat, corn or rice, from legumes such as white lentil, from tubers such as potato or cassava, tapioca starches; dextrins, such as corn dextrins; an example that may especially be mentioned is the rice starch Remy DR I® sold by the company Remy; Amidon de Maïs B® from the company Roquette; potato feculent modified with 2-chloroethylaminodipropionic acid neutralized with sodium hydroxide, sold under the name Structure Solanace® by the company National Starch; native tapioca starch powder sold under the name Tapioca Pure® by the company National Starch;
- dextrins, such as dextrin extracted from corn under the name Index® from the company National Starch;
- celluloses and derivatives thereof, in particular alkyl- or hydroxyalkyl celluloses; mention may be made especially of methylcelluloses, hydroxyalkylcelluloses, ethylhydroxyethylcelluloses and carboxymethylcelluloses. Examples that may be mentioned include the cetylhydroxyethylcelluloses sold under the names Polysurf 67CS® and Natrosol Plus 330® from Aqualon;
- and mixtures thereof.

Preferentially, the hydrophilic gelling agent is chosen from xanthan gums, modified or unmodified starches, celluloses and derivatives thereof, and mixtures thereof.

Said hydrophilic gelling agent(s), different from the AMPS® copolymer described above, may be present in the composition according to the invention in a content ranging from 0.01% to 5% by weight, preferably from 0.1% to 2% by weight, relative to the total weight of the composition.

Solvents

The composition according to the invention may comprise water in a content of greater than or equal to 20% by weight relative to the total weight of the composition.

Preferably, the composition comprises water in a total amount of between 20% and 90% by weight, better still between 30% and 80% by weight, relative to the total weight of the composition.

The composition according to the invention may also comprise one or more organic solvents different from the fatty substances described above.

Examples of organic solvents that may be mentioned include lower $C_1$-$C_4$ alkanols, such as ethanol and isopropanol; polyols and polyol ethers, for instance 2-butoxyethanol, propylene glycol, propylene glycol monomethyl ether and diethylene glycol monoethyl ether and monomethyl ether, and also aromatic alcohols, for instance benzyl alcohol or phenoxyethanol, and mixtures thereof.

Preferably, the composition according to the invention comprises one or more organic solvents, different from the fatty substances described above.

The organic solvent(s) may be present in proportions preferably inclusively between 0.1% and 20% by weight approximately relative to the total weight of the composition, more preferentially between 0.3% and 15% by weight approximately and even more particularly inclusively between 0.5% and 12% by weight relative to the total weight of the composition.

Additives

The composition according to the invention may also comprise cosmetic adjuvants chosen from deodorant active agents, desquamating agents, antimicrobial agents, moisturizers, calmatives, antioxidants, astringents, anti-ageing agents, antiwrinkle agents; softeners, antioxidants, stabilizers, UV-screening agents, vitamins, bactericides, preserving agents, dyes, fragrances or any other ingredient usually used in cosmetics for this type of application, and mixtures thereof.

Needless to say, those skilled in the art will take care to select this or these optional additional compounds such that the advantageous properties intrinsically associated with the cosmetic composition in accordance with the invention are not, or are not substantially, adversely affected by the envisaged addition(s).

Presentation Form

The composition according to the invention may especially be in the form of a suspension, a dispersion, a gel, an emulsion, especially an oil-in-water (O/W) or water-in-oil (W/O) emulsion, or a multiple emulsion (W/O/W or polyol/O/W or O/W/O), in the form of a cream, a mousse, a stick, a dispersion of vesicles, especially of ionic or non-ionic lipids, or a two-phase or multi-phase lotion.

Preferably, the composition according to the invention is in the form of an oil-in-water (O/W) emulsion.

Those skilled in the art may select the appropriate presentation form, and also the method for preparing it, on the basis of their general knowledge, taking into account firstly the nature of the constituents used, in particular their solubility in the support, and secondly the intended application of the composition.

Preferably, the composition according to the invention comprises a "physiologically acceptable medium". The term "physiologically acceptable medium" is intended to mean a medium that is suitable for the topical administration of a composition, and that is compatible with all human keratin materials, such as the skin, the lips, the nails, the mucous membranes, the eyelashes, the eyebrows, the scalp and/or the hair, or any other area of bodily skin.

According to the invention, a physiologically acceptable medium is preferentially a cosmetically acceptable medium, i.e. a medium which is free of any odour or unpleasant appearance and which is entirely compatible with the topical administration route.

More particularly, the composition according to the invention is suitable for topical administration, that is to say for application to the surface of the keratin material under consideration, such as the skin under consideration.

The compositions according to the invention are preferentially cosmetic compositions for caring for and/or making up the skin.

These compositions are in particular intended for topical application to the face and/or the body.

In particular, the composition is applied to the areas of the face, in particular the T area (forehead, nose, cheeks and chin), in particular the forehead and the nose, exhibiting shiny skin.

In one preferred embodiment of the invention, the composition according to the invention has a pH of between 4 and 7, preferably of between 4.5 and 6.5.

The cosmetic compositions according to the invention having a pH of between 4 and 7, preferably having a pH of between 4.5 and 6.5, have improved stability, in particular with regard to the chemical ingredients present in said compositions.

According to one preferred embodiment, the composition according to the invention comprises the combination of a copolymer of 2-acrylamido-2-methylpropanesulfonic acid which is preferably totally salified in the form of an ammonium salt, and of ethoxylated (25EO) stearyl methacrylate, and of n-stearoyl-L-glutamic acid mono sodium salt; with a mixture of cetylstearyl alcohol/cetylstearylglucoside, of arachidyl alcohol and of behenyl alcohol/arachidyl glucoside.

Another subject of the invention is a process for the cosmetic treatment of keratin materials, comprising the application to said keratin materials of a composition as defined above.

Another subject of the invention is also the use of a composition as defined above, for the cosmetic treatment of keratin materials.

The present invention will now be described more specifically by means of examples, which do not in any way limit the scope of the invention. However, the examples make it possible to support specific features, variants and preferred embodiments of the invention.

EXAMPLES

In the examples, the temperature is given in degrees Celsius and corresponds to ambient temperature (20-25° C.), unless otherwise indicated, and the pressure is atmospheric pressure at sea level, unless otherwise indicated. Moreover, unless otherwise indicated, the percentages are expressed on a weight basis relative to the total weight of the composition.

Example 1

The following compositions were prepared according to the process below:

phase B is mixed using a stirrer (for example Maxilab Turbotest tank bottom rotor/stator turbine sold by the company OLSA) at a speed of 800 revolutions/minute while heating at 85° C. for 10 minutes until the solution is homogeneous, phase A is introduced into phase B using the stirrer at a speed of 3000 revolutions/minute while maintaining a temperature of 85° C., phase C is introduced into the mixture of phases A+B using the stirrer at a speed of 3000 revolutions/minute, without heating, until the solution is homogeneous, phase D is then introduced into the mixture of phases A+B+C. The stirring is continued at a speed of 2000 revolutions/minute in order to obtain good homogenization.

TABLE 1

|   | Chemical name (INCI Name) | Composition A (Invention) | Composition B (Invention) | Composition C (Comparative) |
|---|---|---|---|---|
| A | Water | qs 100 | qs 100 | qs 100 |
|   | Glycerol | 5 | 5 | 5 |
|   | Preserving agents | qs | qs | qs |
| B | Cetearyl alcohol (and) Cetearyl glucoside (Montanov 68 from SEPPIC, 80/20) | 2 | 2 | 2 |
|   | Arachidyl alcohol (and) Behenyl alcohol (and) Arachidyl glucoside (Montanov 202 from SEPPIC, 55/30/15) | 2 | 2 | 2 |

TABLE 1-continued

| | Chemical name (INCI Name) | Composition A (Invention) | Composition B (Invention) | Composition C (Comparative) |
|---|---|---|---|---|
| | Sodium stearoyl glutamate (Amisoft HS 11 PF from Ajinomoto) | 0.4 | 0.4 | — |
| | *Copernicia cerifera* (carnauba) wax | 1 | 1 | 1 |
| | Hydrogenated cocoyl glycerides | 2 | 2 | 2 |
| | *Mangifera indica* (mango) seed butter | 2 | 2 | 2 |
| | Dicaprylyl carbonate | 4 | 4 | 4 |
| | *Simmondsia chinensis* (jojoba) seed oil | 2.8 | 2.8 | 2.8 |
| | *Persea gratissima* (avocado) oil | 2.4 | 2.4 | 2.4 |
| C | Ammonium acryloyldimethyltaurate/steareth-25 methacrylate crosspolymer (Aristoflex HMS from Clariant) | 0.3 | 0.3 | 0.3 |
| | Carbomer (Carbopol Ultrez 10 Polymer from Lubrizol) | 0.3 | — | 0.3 |
| | Xanthan gum | — | 0.3 | — |
| D | *Schizandra sphenanthera* fruit extract | 0.1 | 0.1 | 0.1 |
| | *Cyathea medullaris* leaf extract | 0.1 | 0.1 | 0.1 |

The viscosity of compositions A, B and C was analysed using the method described below.

Compositions A1 and A2 are identical, in terms of compounds, to composition A according to the invention with a different acyl glutamic acid salt (sodium stearoyl glutamate) (see Table 2).

Control of the Viscosity:

The viscosity of the compositions is measured using a Rheomat R180 viscometer. The measurements are performed after a resting period of 24 hours, at ambient temperature (25° C.) using the M4 spindle provided with the measuring device. The measurements are performed at controlled ambient temperature (25° C.).

The viscosity of the compositions was analysed at 30 seconds and at 10 minutes.

Results of the Viscosity of the Compositions:

TABLE 2

| Compositions | Sodium stearoyl glutamate (Amisoft HS 11 PF from Ajinomoto) concentration (in g %) | Viscosity at 30 s (in poise) | Viscosity at 10 minutes (in poise) |
|---|---|---|---|
| C (comparative) | 0 | 72 | 65 |
| B (Invention) | 0.4 | 28 | 24 |
| A1 (invention) | 0.15 | 66 | 48 |
| A2 (invention) | 0.25 | 55 | 48 |
| A (invention) | 0.4 | 50 | 42 |

The compositions according to the invention (A, A1, A2 and B) comprising an acyl glutamic acid or a salt thereof at different concentrations have a lower viscosity at 30 seconds and at 10 minutes than the comparative composition not comprising acyl glutamic acid or a salt thereof. Thus, the compositions according to the invention have an appearance that is not very "pasty" and they are easier to take up and to apply while the same time being more pleasant at the time of application.

Control of the Sensory and Cosmetic Properties:

Compositions A, B and C according to the invention are applied to the skin, in a proportion of 1 ml of product on the hand, making circular movements 5 times with the index finger and while subsequently evaluating the application of the formulae, by a panel of 5 individuals.

Compositions A and B according to the invention have an appearance that is not very "pasty", and are therefore easy to apply. Furthermore, there is barely a soaping effect observed on the skin during the application of the compositions according to the invention.

Comparative composition C exhibits a very considerable soaping effect on the skin compared with the compositions according to the invention.

Control of the Stability of the Compositions:

The stability of a composition of the invention can be evaluated by means of the following protocol.

A composition is prepared and is then placed at ambient temperature, in an incubator at a temperature of 4° C., in an incubator at a temperature of 37° C. and in an incubator at a temperature of 45° C. (for example an incubator of the Firlabo Bio concept brand).

At T=0, the pH is evaluated and the viscosity is measured for each composition, and also the appearance, colour and odour of the composition. Each composition is also observed under a microscope between a cover slip and slide, at a magnification of ×10.

At T=1 month, the appearance, colour and odour of each composition is evaluated. Each composition is also observed under a microscope between a cover slip and slide, at a magnification of ×10. Its microscopic appearance must remain close to the initial appearance.

At T=2 months, the pH is evaluated and the viscosity is measured for each composition, and also the appearance, colour and odour of the composition. Each composition is also observed under a microscope between a cover slip and slide, at a magnification of ×10. Its microscopic appearance must remain close to the initial appearance.

The composition must not exhibit any modification of the macroscopic appearance: it must remain smooth and homogeneous, without any release, without any phase separation and without any colour change.

Compositions A and B according to the invention do not exhibit any macroscopic or microscopic appearance modifications; they are considered to be stable.

Comparative composition C exhibits stability problems after 2 months spent in the incubator at 45° C.

Example 2

The following compositions were prepared according to the process as described in example 1.

TABLE 3

| | Chemical name (INCI Name) | Composition D (Invention) | Composition E (Comparative) |
|---|---|---|---|
| A | Water | qs 100 | qs 100 |
| | Glycerol | 5 | 5 |
| | Preserving agents | qs | qs |
| B | Cetearyl alcohol (and) Cetearyl glucoside (Montanov 68 from SEPPIC, 80/20) | 2 | 2 |
| | Arachidyl alcohol (and) Behenyl alcohol (and) Arachidyl glucoside (Montanov 202 from SEPPIC, 55/30/15) | 2 | 2 |
| | Sodium stearoyl glutamate (Amisoft HS 11 PF from Ajinomoto) | 0.4 | 0.4 |
| | *Copernicia cerifera* (carnauba) wax | 1 | 1 |
| | Hydrogenated cocoyl glycerides | 2 | 2 |
| | *Mangifera indica* (mango) seed butter | 2 | 2 |
| | Dicaprylyl carbonate | 4 | 4 |
| | *Simmondsia chinensis* (jojoba) seed oil | 2.8 | 2.8 |
| | *Cocos nucifera* oil (and) *gardenia taitensis* flower | 2.4 | 2.4 |
| | *Persea gratissima* (avocado) oil | 2.4 | 2.4 |
| C | Ammonium acryloyldimethyltaurate/steareth-25 methacrylate crosspolymer (Aristoflex HMS from Clariant) | 0.3 | — |
| | Carbomer (Carbopol Ultrez 10 Polymer from Lubrizol) | 0.3 | 0.3 |
| D | *Schizandra sphenanthera* fruit extract | 0.1 | 0.1 |
| | *Cyathea medullaris* leaf extract | 0.1 | 0.1 |
| | Hydrolyzed linseed extract | 1 | 1 |

Control of the Sensory and Cosmetic Properties:

Composition D according to the invention and comparative composition E are applied to the skin, in a proportion of 1 ml of product on the hand, making circular movements 5 times with the index finger and while subsequently evaluating the application of the formulae, by a panel of 5 individuals.

Composition D according to the invention have an appearance that is not very "pasty", and are therefore easy to apply. Furthermore, there is barely a soaping effect observed on the skin during the application of the composition according to the invention.

Comparative composition E exhibits a very considerable soaping effect on the skin compared with the composition D according to the invention.

The invention claimed is:

1. A composition comprising:
   a) at least one copolymer comprising at least one 2-acrylamido-2-methylpropane sulfonic acid monomer and at least one monomer bearing a hydrophobic group monomer chosen from the acrylates and acrylamides of formula (II):

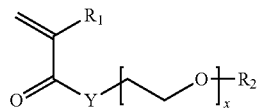

(II)

in which R1 denotes a hydrogen atom or a linear or branched C1-C6 alkyl radical; Y denotes O or NH; R2 denotes a hydrocarbon-based radical comprising from 6 to 50 carbon atoms; and x denotes a number ranging from 0 to 100,
   b) at least one acyl glutamic acid or a salt thereof, and
   c) at least one emulsifying system comprising at least one alkyl polyglucoside.

2. The composition according to claim 1, wherein the a) at least one copolymer is crosslinked by a crosslinking agent.

3. The composition according to claim 1, wherein the at least one 2-acrylamido-2-methylpropanesulfonic acid monomer is completely salified.

4. The composition according to claim 1, wherein, in formula (II), Y denotes an oxygen atom, the group R1 represents a methyl, the group R2 represents an alkyl radical comprising from 12 to 18 carbon atoms, and x represents an integer between 3 and 25.

5. The composition according to claim 1, wherein the monomer bearing a hydrophobic group of formula (II) is ethoxylated (25EO) stearyl methacrylate, corresponding to the compound of formula (II) in which the group R1 represents a methyl, the group Y denotes O, the group R2 represents an alkyl radical comprising 18 carbon atoms and x is equal to 25.

6. The composition according to claim 1, wherein the a) at least one copolymer is a copolymer of 2-acrylamido-2-methylpropanesulfonic acid and of ethoxylated stearyl methacrylate (25EO).

7. The composition according to claim 1, wherein the a) at least one copolymer are present in the composition in a content ranging from 0.01% to 10% by weight relative to the total weight of the composition.

8. The composition according to claim 1, wherein the b) at least one acyl glutamic acid is chosen from acyl glutamic acids in which the acyl group comprises from 10 to 30 carbon atoms.

9. The composition according to claim 1, wherein the salt(s) of the b) at least one acyl glutamic acid is chosen from the salts of alkali metals, the salts of alkaline-earth metals, or the ammonium salts of said acids.

10. The composition according to claim 1, wherein the b) at least one acyl glutamic acid or salt thereof is chosen from lauroyl glutamic acids, cocoyl glutamic acids, sodium stearoyl glutamate, potassium lauroyl glutamate, potassium cocoyl glutamate, sodium olivoyl glutamate and mixtures thereof.

11. The composition according to claim 1. wherein the b) at least one acyl glutamic acid or salt thereof is present in the composition in a content ranging from 0.01% to 5% by weight relative to the total weight of the composition.

12. The composition according to claim 1, wherein the b) at least one acyl glutamic acid is chosen from the compounds of formula (IV) below:

$$R_1O\text{-}(G)_a \qquad (IV)$$

in which:
   R1 denotes a linear or branched alkyl radical comprising from 6 to 30 carbon atoms;
   the group G is a saccharide residue;
   a is a number ranging from 1 to 10.

13. The composition according to claim 12, wherein the saccharide residue is chosen from glucose, dextrose, saccharose, fructose, galactose, maltose, maltotriose, lactose, cellobiose, mannose, ribose, dextran, talose, allose, xylose, levoglucan, cellulose, starch, and mixtures thereof.

14. The composition according to claim 1, wherein the at least one alkyl polyglucoside is chosen from the arachidyl alcohol and behenyl alcohol/arachidyl glucoside mixture, the cetylstearyl alcohol/cetylstearyl glucoside mixture, and mixtures thereof.

15. The composition according to claim 1, wherein the composition comprises at least one fatty substance.

16. The composition according to claim 1, wherein the composition comprises at least one crosslinked (meth) acrylic acid homopolymer.

17. The composition according to claim 1, wherein the composition comprises at least one hydrophilic gelling agent chosen from xanthan gums, modified or unmodified starches, celluloses and derivatives thereof, and mixtures thereof.

18. A process for the cosmetic treatment of keratin material, in which a composition as defined according to claim 1 is applied to said keratin material.

19. The process according to claim 18, for the cosmetic treatment of keratin material wherein the keratin material is selected from the group of the scalp, the hair and the skin.

* * * * *